United States Patent [19]

Turcotte et al.

[11] 4,038,142

[45] July 26, 1977

[54] ISOLATION AND CHARACTERIZATION OF PHENOTYPES OF MYCOBACTERIA

[75] Inventors: Raymond Turcotte, Montreal; Marc Quevillon, Ville D'Anjou, both of Canada

[73] Assignee: Institut Armand Frappier, Ville de Laval, Canada

[21] Appl. No.: 582,376

[22] Filed: May 30, 1975

[51] Int. Cl.$^2$ ................................................ C12K 1/04
[52] U.S. Cl. ..................................... 195/96; 424/92; 424/93
[58] Field of Search .................. 195/103.5 R, 59, 79, 195/94–102, 103.5 A; 424/92, 93

[56] References Cited

U.S. PATENT DOCUMENTS

| 3,135,663 | 6/1964 | Muggleton et al. | 424/92 |
| 3,567,585 | 3/1971 | Block et al. | 195/96 |

OTHER PUBLICATIONS

Bergey's Manual of Determinative Bacteriology, 8th Ed., The Williams & Wilkins Co., Baltimore, 1974, pp. 682–684.
Lamanna et al. "Basic Bacteriology," Ed., Waverly Press, Inc. Baltimore, Md., pp. 584–589.
Jordan et al. "Textbook of Bacteriology," 14th Ed., Press of W. B. Saunders Co., Philadelphia, 1947, pp. 21–23.

*Primary Examiner*—Alvin E. Tanenholtz
*Assistant Examiner*—C. A. Fan
*Attorney, Agent, or Firm*—Burgess, Dinklage & Sprung

[57] ABSTRACT

The disclosure relates to a process of preparing a culture of mycobacteria by culturing mycobacteria on a liquid medium capable of dissociating mycobacteria into phenotypes, the culturing being carried out under partial anaerobic conditions and at a pH between 4.5 and 8.5.

3 Claims, 9 Drawing Figures

Phenotype 1

Phenotype 2

Phenotype 3

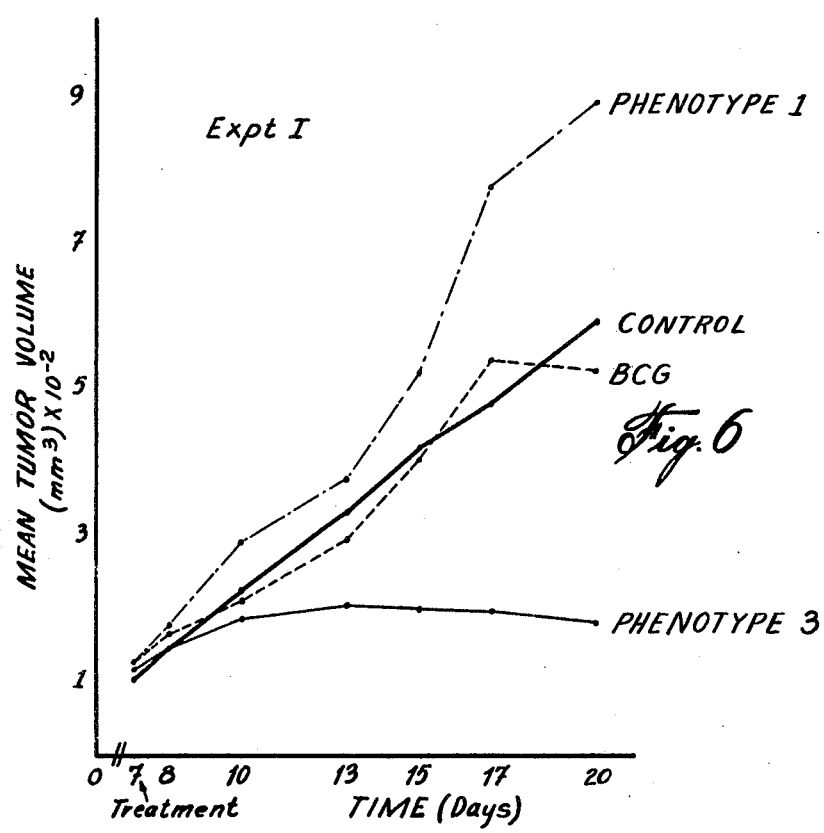
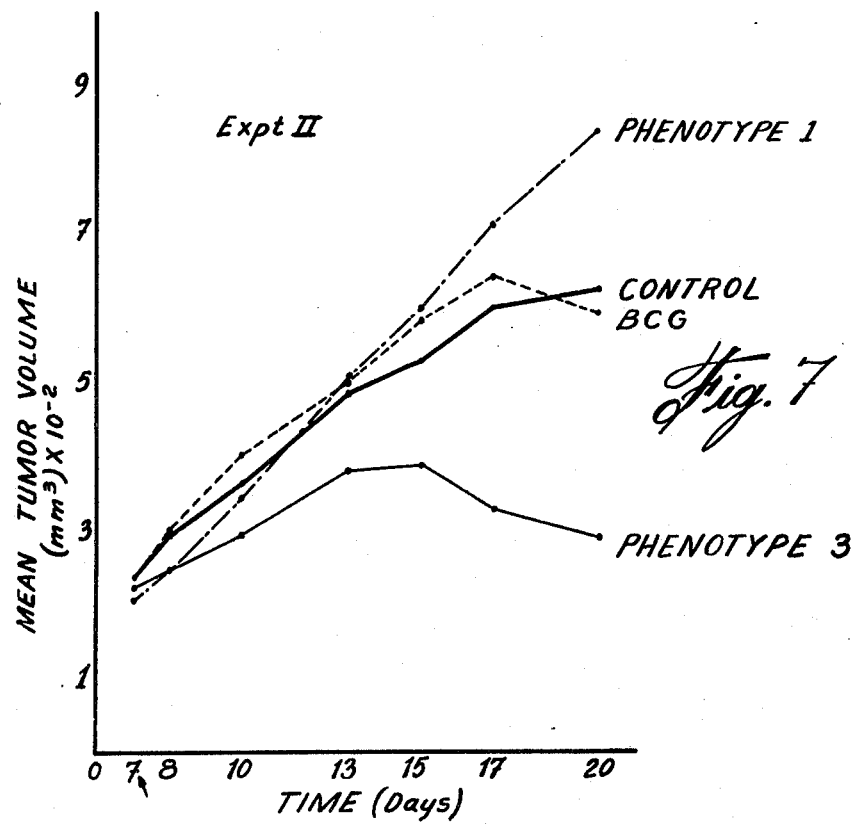

ISOLATION AND CHARACTERIZATION OF PHENOTYPES OF MYCOBACTERIA

BACKGROUND OF THE INVENTION

1. Field of the Invention

This invention relates to a process of dissociating a culture of mycobacteria on liquid media. More particularly, the present invention relates to the production of phenotypes of mycobacteria, at least two of which have been found to possess interesting biological activities.

2. Description of the Prior Art

As early as 1927, Petroff (Microbic dissociation: the tubercle bacillus Proc. Soc. Exp. Biol. Med., 24: 632-634) has shown that several types of tubercle bacilli dissociated into 2 distinct variants when cultured on the solid gentian-violet-egg medium: the so-called rough and smooth colonies. In subsequent years, and more recently, the dissociation phenomenon of mycobacteria has been confirmed repeatedly. With the advent of transparent solid media, the previous classification into rough and smooth variants was further subdivided into Rough C, R, F, etc, and Smooth S, D, T, etc, based on the microscopic characteristics of colonies. Some of these colonial forms appear to be specific for a given species of tubercle bacilli and of atypical mycobacteria; they can thus be of value in early identification. Other investigators working mainly with BCG substrains, have described the spreading, intermediate and non-spreading types of colonies.

Investigations have so far shown that there is no conclusive proof that the different colonial forms represent true mutations of mycobacteria. However, many factors such as the composition of solid media, cultural conditions, etc., can influence colony morphology. Thus, it would appear that the dissociation phenomenon represents changes in the phenotype of mycobacteria.

Early investigations had shown that differences in the protein, glycogen, carbohydrate, and lipid contents exist between the rough and smooth variants of a few strains of mammalian tubercle bacilli. However, the relationship between these constituents and the colonial forms is still not well defined. More recently, Fregnan et al. have reported a good correlation between the mycoside content and the colony morphology of atypical mycobacteria.

It is an object of the present invention to provide a process whereby mycobacteria are dissociated into phenotypes.

It is another object of the present invention to provide conditions under which mycobacteria are cultured to produce phenotypes thereof.

SUMMARY OF THE INVENTION

These and other objects of the invention can be attained by culturing mycobacteria on a liquid medium capable of promoting the growth of the mycobacteria, the culturing being carried out under partial anaerobic conditions and at a pH between 4.5 and 8.5.

The mycobacteria which can be used in the process according to the invention may include the following well known strains of microorganisms: all substrains of Bacillus Calmette-Guerin (BCG), M. tuberculosis (H37Rv), M. kansasii (P-8), a scotochromogen (P-5) and M. intracellulare (P-2). Those strains of microorganisms are all readily available to the public from well-known depositories. For example, they can be found at the ATCC and are also available to the public at the Institut de Microbiologie et d'Hygiene de Montreal, of Montreal, Canada.

Although any liquid medium which can promote the growth of mycobacteria can be used according to the invention, the following media are preferred:
1. Sauton's medium;
2. Long's medium;
3. Proskauer and Beck's medium;
4. Middlebrook's medium.

According to the invention, the culturing is preferably carried out at a temperature of about 37.5° C. during about 14 to 21 days.

The process according to the invention may be adapted to obtain surface bacterial pellicles consisting of a mixture of smooth, filamentous and rough bacterial islets, respectively constituting Phenotype 1, 2 and 3 of the mycobacteria.

After the bacterial pellicles are obtained, they can be separately sub-cultured into Phenotypes 1, 2 and 3 in the same liquid medium followed by isolation of each of the Phenotypes 1, 2 and 3 in pure state.

It is thereafter possible to separately effect several passages of each Phenotypes 1, 2 and 3 on the liquid medium. Preferably, four such passages are used.

Finally each Phenotype can be isolated from the mixture of Phenotypes 1, 2 and 3.

BRIEF DESCRIPTION OF THE DRAWINGS

The invention will be illustrated by means of the following drawings, in which:

FIG. 6 represents curves of the mean tumor volume after treatment of ascites nodules with BCG, Phenotype 1, Phenotype 3 and Sauton's medium.

FIG. 7 is the same as FIG. 6 except that it shows the results of a second experiment.

DESCRIPTION OF THE PREFERRED EMBODIMENT

Microorganisms used

Species of mycobacteria included the Montreal substrain of Bacillus Calmette-Guerin (BCG), M tuberculosis (H37Rv), M. kansasii (P-8), one scotochromogen (P-5) and M. intracellulare (P-2 which as stated above are easily available. All these strains were maintained on glycerin potato slants.

Preparation Of Microorganisms Before Use

Prior to their use the bacilli were cultured as surface pellicle on Sauton's medium (125 ml) contained in 250 ml flat bottom flasks. The seeded flasks were closed as usual with a cotton plug and incubated at 37.5° C.

Induction Of Phenotypes

Figure 1:
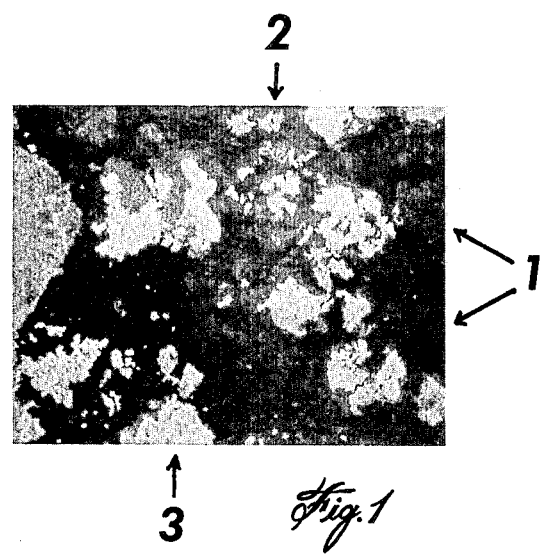
FIG. 1 is a view of the surface growth of BCG showing the mixture of smooth, filamentous and rough bacterial islets

Small inocula withdrawn from the flat bottom flasks were used to seed the surface of 50 ml of Sauton's medium (pH 7.2) contained in 200 ml culture glass bottles (Cabinet Oval, Dominion Glass, Montreal, Canada). The bottles were tightly closed with a Bakelite screwcap and incubated on their flat side at 37.5° C during 14 to 21 days. The bottles were observed every 2-3 days in order to note the morphological characteristics of the developing surface pellicles during the incubation period. Instead of the uniformly rough pellicle which characterized after the incubation period, the surface growth of mycobacteria in flat bottom flasks, the surface growth in bottles consisted of a mixture of smooth, filamentous and rough bacterial islets as shown in FIG. 1 of the drawings. This phenomenon occurred spontaneously sometimes after the first passage in these experimental conditions but more frequently after the 2nd or 3rd passage. Moreover, it has been observed with all the mycobacterial strains used, i.e. with BCG, M. tuberculosis H37Rv and 3 representative strains of atypical mycobacteria.

The bacilli isolated from each of these islets will hereafter be referred to as Phenotypes 1, 2 and 3, respectively.

Other liquid media such as the Long's, the Proskauer and Beck's and the Middlebrook's media gave similar results. However, with Long's medium the relative proportion of smooth islets was increased by comparison with the other 2 media for corresponding subcultures of similar ages.

When the culture bottles containing the Sauton's medium were closed with a cotton plug instead of a screw cap, mycobacteria did not dissociate into phenotypes; flat bottom flasks tightly closed with a rubber stopper inhibited almost completely the bacterial growth. This should clearly establish that the process according to the invention should strickly be carried out under partial anaerobic conditions.

Isolation And Purification Of The Phenotypes

Selected inocula originating from the smooth, filamentous and rough bacterial islets were then subcultured on Sauton's medium (pH7.2) contained in 3 series of culture bottles. In these conditions, Phenotype 1 was readily isolated in a pure state and it was maintained as such by sequential passages at 14 days intervals. In contrast, Phenotypes 2 and 3 were always contaminated to some extent with Phenotype 1 even after several passages under the same experimental conditions.

Figure 2A:
FIGS. 2A, 2B and 2C are individual views of morphological patterns of the surface growth of Phenotypes 1, 2 and 3 isolated from BCG.
Figure 2B:
Figure 2C:
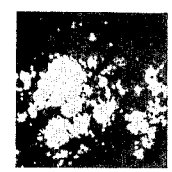

FIG. 2 illustrates the morphological patterns of the surface pellicles of the 3 phenotypes of BCG after purification by sequential passages. Phenotype 1 derived from the smooth bacterial islets shown in FIG. 1 and gave a very thin and uniform pellicle that covered all the surface of the culture medium and after 14 to 16 days of incubation climbed along the sides of the glass bottle. Phenotype 2 may be derived from 2 sources; it can be isolated directly from the filamentous bacterial islets as shown in FIG. 1 by selecting appropriate inoculum. It has also frequently been observed that Phenotype 1 loses its morphologic characteristics after 3 to 4 passages and converts spontaneously into Phenotype 2. The surface pellicle of Phenotype 2 was characterized by the presence of long and tortuous bacterial filaments. In old cultures (21 days) these filaments became broader and can cover all the surface of the medium. This phenotype was not stable since after 5 to 6 passages it frequently converted into Phenotype 3. The surface growth of Phenotype 3 was constituted by rough bacterial clumps of variable sizes which, even in old cultures, never covered all the surface of the liquid medium. Like Phenotype 2, it was not stable since on a few occasions Phenotype 3 has converted into Phenotype 2. As seen in FIG. 2, both Phenotypes 2 and 3 were contaminated to some extend with Phenotype 1.

These 3 phenotypes were isolated in this manner from all strains of mycobacteria listed above. Furthermore, all three phenotypes possessed the staining properties of mycobacteria as demonstrated by the Zielh-Neelsen technique.

It should be emphasized that after their isolation, the 3 phenotypes were cultured on Sauton's medium contained in flat bottom flasks; in these conditions, all three phenotypes lose gradually their growing characteristics in such a way that after 3 to 4 passages they had completely reverted to the original strain. Moreover, after completion of the reverting phase, the 3 phenotypes can be isolated again from each revertant.

Bacterial Growth Curves Of Phenotypes 1 and 3

Two series of culture bottles were first inoculated respectively with Phenotypes 1 and 3. After various periods of incubation (up to 24 days) at 37.5° C, groups of 3 bottles, chosen at random, were removed from the incubator and their pooled content was filtered on a Buckner funnel. The bacillary mass was dried till constant weight in an oven at 110° C. The yield of dry bacilli was calculated as mg per 100 ml of Sauton's medium.

Figure 3:
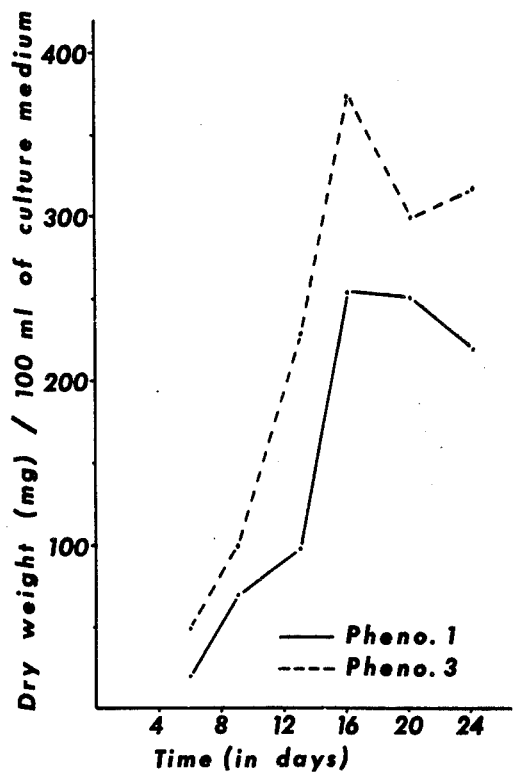
FIG. 3 shows bacterial growth curves of Phenotype 1 and Phenotype 3 isolated from BCG.

FIG. 3 shows the growth curved (pool data from 2 independent experiments) obtained with Phenotype 1 and Phenotype 3 isolated from BCG and cultured on Sauton's medium at pH 7.2. Although the lag phase was a little longer for Phenotype 1, the rate of growth was about the same for both phenotypes. Moreover, during all the incubation period the yield of Phenotype 3 was larger than that of Phenotype 1.

A large batch of Sauton's medium was prepared and divided into 10 lots. Each lot was adjusted to the desired pH (from 4.5 to 9.0 with an encreament of 0.5) with concentrated NH4OH prior to its distribution into culture bottles. Each series of bottles was first respectively seeded with inocula of both phenotypes grown on Sauton's medium at pH 7.2 and, for the next 3 passages, with the phenotypes growing at the appropriate pH. The yield of dry bacilli (mean value of these 3 passages) in mg per 100 ml of medium at each specified pH was determined to evaluate the results.

The pH of culture filtrates following the incubation period of 14 days in closed culture bottles drop from 7.2 to 6.7, whereas in flat bottom flasks, it increased slightly to 7.3-7.4. On the other hand, no difference in the drop of pH was observed between Phenotype 1 and Phenotype 3 after the incubation period.

Figure 4:
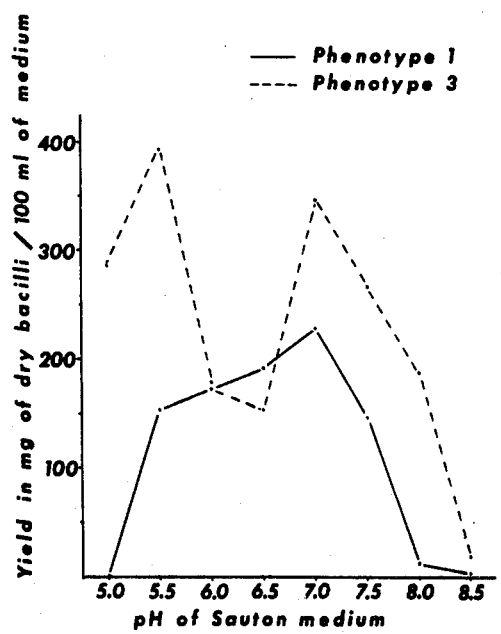
FIG. 4 shows the influence of pH of Sauton's medium on the growth of Phenotypes 1 and 3 isolated from BCG.

The influence of pH of Sauton's medium on the growth of Phenotype 1 and Phenotype 3 of BCG is shown in FIG. 4. As seen, Phenotype 1 grew well on Sauton's medium at pH between 5.5 and 7.5; with a maximum growth at pH 7.0. On the contrary, 2 peaks of bacterial growth were observed with Phenotype 3: one at pH 5.5 and other at pH 7.0. Moreover, Phenotype 3 grew well at pH as low as 5.0 and as high as 8.0. The higher yield of Phenotype 3 at pH 7.0 confirmed the data shown in FIG. 3.

After an incubation period of 14 days, Phenotypes 1 and 3 obtained from a pool of at least 10 culture bottles were isolated by filtration, washed with distilled water, weighted and disintegrated in a ball mill as described by R Turcotte in 1969 in Can. J. Microbiol., 15: 35–41. The bacillary debris were removed by centrifugation at 10,000 X g for half an hour and the supernatant was further centrifuged at 144,000 X g for 3 h. The clear supernatant was dialyzed exhaustively against distilled water and lyophilized. The yield of mycobacterial components was expressed as mg of lyophilized products per gram (moist weight) of bacilli.

The protein and carbohydrate composition of Phenotypes 1 and 3 isolated from five mycobacteria are presented in Table 1.

TABLE 1
PROTEIN AND CARBOHYDRATE CONTENTS OF PHENOTYPES 1 AND PHENOTYPES 3 ISOLATED FROM MYCOBACTERIA

| STRAIN | PHENO-TYPE | PROTEIN[a] | CARBO-HYDRATE[a] |
|---|---|---|---|
| BCG | 1 | 51.9[b] | 25.3[b] |
|  | 3 | 44.7 | 28.3 |
| H37Rv | 1 | 54.5 | 17.4 |
|  | 3 | 54.1 | 14.6 |
| M. kansasii | 1 | 38.3 | 32.3 |
|  | 3 | 36.5 | 26.6 |
| Scotochromogen | 1 | 44.7 | 28.4 |
|  | 3 | 41.3 | 25.3 |
| M. intra-cellulare | 1 | 42.9 | 26.0 |
|  | 3 | 46.1 | 21.7 |

[a]Protein and carbohydrate concentrations were determined by the micro-Kjelkahl technique and the thymolsulfuric acid reaction, respectively.
[b]in percent of dry bacilli. Each data represents a mean value obtained from at least 2 separate experiments.
N.B. All cultures were 14 day-old. For Phenotypes 3, the chemical analyses were done on bacilli selected from the rough bacterial islets.

Total nitrogen content of entire bacilli was estimated by the micro-Kjeldahl method and converted to proteins using a conversion factor of 6.25. The protein content of hydrosoluble extracts was determined by the method of Lowry et al. Crystalline bovine albumin (Armour and Co., Chicago, Ill.) was used as standard. Carbohydrates were determined by the thymol-sulfuric acid reaction as modified by Shetlar and Masters. D-glucose was the standard. Before the determination of carbohydrates in the entire mycobacterial cells, the bacilli were hydrolyzed in 2N for 2 h at 100° C as described previously.

As seen, with the exception of M. intracullare, Phenotypes 1 contained a little more nitrogenous components than Phenotypes 3. Moreover, both M. kansasii phenotypes possessed less nitrogen than those of other mycobacteria. Higher carbohydrate contents were also found for Phenotypes 1, with the exception of BCG. Moreover, the carbohydrate concentration in H37Rv phenotypes was the lowest, whereas it was approximately the same for the other strains.

Phenotypes from a few strains of mycobacteria were disintegrated mechanically and the yield of hydrosoluble extracts, as well as their chemical composition, were determined.

TABLE 2
YIELD AND CHEMICAL COMPOSITON OF HYDROSOLUBLE COMPONENTS EXTRACTED FROM PHENOTYPES 1 AND 3 OF A FEW STRAINS OF MYCOBACTERIA

| STRAIN | PHENO-TYPE | YIELD | PROTEIN[a] | CARBO-HYDRATE |
|---|---|---|---|---|
| BCG | 1 | 69.9[b] | 55.2[c] | 14.3[c] |
|  | 3 | 52.8 | 56.3 | 17.9 |
| H37Rv | 1 | 64.7 | 47.5 | 13.5 |
|  | 3 | 39.1 | 61.8 | 17.1 |
| M. kansasii | 1 | 40.0 | 42.7 | 21.1 |
|  | 3 | 36.1 | 44.1 | 24.5 |

[a]measured by the method of Lowry et al.
[b]mg of lyophilized product per gram of moist bacilli
[c]in percent of lyophilized product.

It is seen that larger quantities of components can be extracted from Phenotypes 1 than from Phenotypes 3. However, the protein and carbohydrate contents of extracts isolated from Phenotypes 3 were slightly higher than those of Phenotypes 1, which is in contrast with the results obtained with the corresponding entire bacilli (Table 1).

The antigenic composition of mycobacterial phenotypes was determined by the immuno-diffusion technique using antisera directed against the corresponding parental strains. For example, antisera against the soluble extracts isolated from the BCG strain and its 2 phenotypes, from M. tuberculosis H37 Rv and from M. kansasii were produced in rabbits according to an immunization schedule described by R. Turcotte in 1969 in Can. J. Microbiol, 15: 681–688. The micro immuno-diffusion technique of Wadsworth (Int. Arch Allergy, 10: 355-358) as modified by Crowle (J. Lab. Clin. Med., 52: 784–787) was used for comparing the antigenic composition of phenotypes. According to the diffusion patterns, each well of plastic templates was filled with the various bacterial extracts (1% solution) and with undiluted antisera. The plates were incubated at room temperature in a moist atmosphere for 4 days before final reading. After prolonged washing of the plates with saline, they were stained with thiazine red (0.1% in 1.0% acetic acid).

Figure 5:
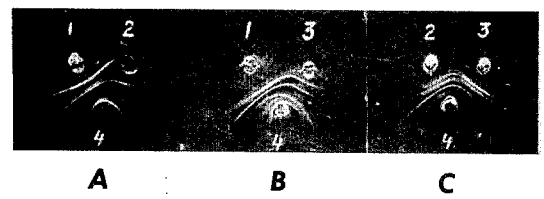
FIGS. 5A, 5B and 5C show precipitation reactions between soluble extracts of BCG, of its 2 phenotypes and BCG antiserum.

FIG. 5 shows the immuno-diffusion patterns obtained with the parental BCG and its 2 phenotypes. As seen in FIG. 5-A, at least 2 antigenic determinants were missing in Phenotype 1 as compared to the parental BCG. Phenotype 3 seemed to possess the same number of antigenic determinants as the parental BCG, though quantitative variations in the concentration of these determinants existed between these 2 preparations (FIG. 5-B). Finally, the antigenic comparison of the 2 phenotypes indicated that Phenotype 3 possessed at least 1 antigen which was absent from Phenotype 1 (FIG. 5-C). Essentially the same results were obtained with the phenotypes from 2 other strains (H37Rv and M. kansasii).

To see if the phenotypes possess distinctive antigens not present in the parental strains, antisera directed against the 2 BCG phenotypes were prepared and absorbed with hydrosoluble extracts of the parental BCG prior to their study by the immuno-diffusion technique against their homologous antigens. The absorption of both types of antisera with extracts of parental BCG led to the disappearance of all the precipitin bands. These results suggest that new antigens were absent in the phenotypes. However, absorption of Phenotype 3 antisera with extracts of Phenotype 1 prior to their reaction against Phenotype 3 antigens led to the disappearance of all but one precipitin bands; thus confirming the results presented in FIG. 5-C.

A suspension (about 1.0%) of Phenotypes 1 and 3 obtained from BCG was homogenized to disrupt bacillary clumps. The negative staining was performed according to the technique of Brenner and Horne (Biochem. Biophys. Acta., 34: 103–110). The grids were examined under an electron microscope (Philips 300) and measurements of bacillary dimensions were done directly on the TV monitor.

On electron microscopic examination, no difference in cell wall structure, size and the number of granules inside the cytoplasm were observed between the parental BCG and its 2 phenotypes. However, the bacillary length of Phenotype 1 was shorter than that of Phenotype 3: $1.37\mu$ as compared to $1.45\mu$, respectively (mean value obtained from 300 measurements). This difference was highly significant ($P<0.001$) when analyzed by the Student "$t$" test.

The culture of several species of mycobacteria on the surface of liquid media under partial anaerobic conditions led to the dissociation of the original strain into 3 phenotypes according to the morphological pattern of their surface growth.

Presently, it is believed that dissociation of mycobacteria into phenotypes was due mostly to the fact that they were growing in semi-anaerobic conditions. Obviously, such conditions were deleterious to the complete development of mycobacteria since the yield of bacilli (in mg/100 ml of medium) in culture bottles was about 4 times less than that obtained in flat bottom flasks. However, even though tubercle bacillus is an obligate aerobe, it can grow in the experimental conditions used in this study.

As will be shown below it has been found that Phenotype 1 enhances whereas Phenotype 3 inhibited the early development of subcutaneous transplants of Ehrlich carcinoma in Swiss mice. Other biological properties of these phenotypes will be published in the near future.

The biological activities of Phenotypes 1 and 3 will be described in the following tests.

Randombred male Swiss mice, 18–22 g, were fed standard commercial diet and water.

Ehrlich carcinoma obtained originally from Dr. Roger Daoust of the Montreal Cancer Institute were maintained routinely, by intraperitoneal passages in Swiss mice at weekly intervals. For the present experiments, ascites cells were harvested in minimal essential medium (MEM) 199, washed 2 or 3 times in that medium, and adjusted to the desired concentration after cellular counting. Mice were inoculated sc in the lower left ventral quadrant with $1 \times 10^7$ cells in a volume of 0.1 ml and distributed, at random, in groups of 8. This site was chosen, instead of the back of the animal, to evaluate the effects of BCG on the extension of the tumor into the peritoneal cavity.

The parental BCG, and 2 phenotypes (1 and 3) derived from it, were used. All 3 microorganisms were 14 days old when harvested. Suspensions of bacilli, containing 10 mg (moist weight)/ml Sauton medium 1:4, were prepared and kept frozen at $-50°$ C until used. The number of viable U/ml, determined by plate counting on solid Dubos medium, were $13 \times 10^7$, $20 \times 10^7$, and $26 \times 10^7$ for the parental BCG, phenotype 1, and phenotype 3, respectively.

Seven days after the sc transplantation of the ascites cells, 0.1 ml of each bacillary suspension was injected directly into the tumor nodule. Control cancerous mice were inoculated with 0.1 ml Sauton medium diluted 1:4.

Developing tumors were measured every 2–3 days with a caliper, and the volume of the tumor mass was calculated according to the formula used by Attia and Weiss (Cancer Res. 26: 1787–1800, 1966).

The P values were calculated by the Student's $t$ test.

The effects of the 3 preparations of BCG on the early development of sc transplants, as observed in 2 independent experiments shown in FIGS. 6 and 7. During this period of observation, the parental BCG had no effect on tumor growth, when compared to the control group inoculated with Sauton medium. In contrast, phenotype 3 had a marked inhibitory effect on tumor growth. Surprisingly, this inhibitory effect was detectable within the first days of treatment and became more significant at the end of the observation period ($P<0.05$ and $P=0.1$, as compared to controls and parental BCG).

In contrast with phenotype 3 and parental BCG, phenotype 1 enhanced tumor growth and is thus a very useful product in research. This stimulating effect, which seemed to occur early after treatment, was more evident thereafter. However, phenotype 1 differed slightly from controls ($P=0.1$) and not from the parental BCG.

In both experiments, the difference between the effects of phenotypes 1 and 3 on tumor growth, at 17 and 20 days, was highly significant ($P<0.001$).

To eliminate the possibility that the inhibiting and stimulating effects could be due to differences in the size of the local inflammatory reactions induced by the various BCG preparations, groups of normal mice were inoculated sc with similar doses of bacilli as those used in cancerous animals. As expected, small inflammatory reactions were detected at the inoculation sites. However, the size of these reactions and their evolution were the same for all 3 BCG preparations.

After the 20th day, the mice were observed daily for death, tumor regression, and extension of the tumor into the peritoneal cavity. The mean survival time of the control animals was $38.4 \pm 1.22$ days, whereas that of animals treated with parental BCG, phenotype 3, and phenotype 1 was $42.8 \pm 4.05$, $43.1 \pm 4.53$, and $34.8 \pm 2.71$ days, respectively (pooled results of the 2 expts). Statistical analyses of these data revealed that phenotype 3 differed significantly from phenotype 1 ($P<0.05$) and controls ($P<0.05$). Moreover, in both experiments, the group of mice treated with phenotype 1 had the lowest incidence of tumor regression, with most frequent extension of the tumor into the peritoneal cavity. Finally, the effects of phenotype 3 were not significantly different from those of the original BCG.

To see whether similar inhibiting and stimulating effects could be observed when the ascites cells were implanted intraperitoneally (ip), groups of 10 Swiss mice were inoculated first with a mixture containing $10^7$ tumor cells and $10^6$ bacilli (parental BCG, phenotype 1, or phenotype 3) and then treated, 7 days later, with the same dose of the appropriate microorganisms. The results are shown in table 3. In ip transplanted tumors, phenotype 1 as well as phenotype 3 and the parental BCG inhibited the tumor development when compared to controls. However, phenotype 3 appeared to be the most potent inhibitory preparation (phenotype 3 vs. phenotype 1:$P=0.1$).

TABLE 3
EFFECTS OF 3 PREPARATIONS OF BCG ON IP TRANSPLANTS OF ASCITES CELLS IN SWISS MICE

| Mice treated with* | Number of mice with tumoral regression | Mean survival time (days±SE) | P values+ |
|---|---|---|---|
| Parenta BCG | 0/10 | 24.7±2.91 | <0.01 |
| Phenotype 1 | 0/10 | 23.0±2.46 | <0.02 |
| Phenotype 3 | 1/10 | 29.3±3.64 | <0.01 |
| Sauton medium (control) | 0/10 | 15.7±0.87 | |

*At day 0, injection of mixtures of ascites cells and bacilli; at day 7, ip injection of bacilli only.
+When compared to the control group.

We claim:

1. Process which comprises culturing a mycobacteria under partial anaerobic conditions in culture bottles containing a liquid medium selected from the group consisting of Sauton's medium, Long's medium, Proskauer and Beck's medium and Middlebrook's medium, said liquid medium partially filling said culture bottles, said culture bottles being tightly closed and incubated on their flat side at 37.5° C during 14 to 21 days, the pH of said culture medium being maintained between 4.5 and 8.5, said culturing being carried out during about 14 to 21 days, thereby obtaining surface bacterial pellicles consisting of a mixture of smooth, filamentous and rough bacterial islets, respectively constituting Phenotypes 1, 2 and 3 of said mycobacteria, separately subculturing each of said Phenotypes 1, 2 and 3 in new supply of said liquid medium and isolating each of said Phenotypes 1, 2 and 3 in pure state.

2. Process according to claim 1, wherein said mycobacteria are selected from the group consisting of all substrains of Bacillus Calmette-Guerin (BCG), *M. tuberculosis* (H37Rv), *M. kansasii* (P-8), one scotochromogen (P-5) and *M. intracellulare* (P-2).

3. Process according to claim 2, wherein said mycobacteria include all substrains of BCG.

* * * * *